(12) United States Patent
Ahrens et al.

(10) Patent No.: US 7,932,211 B2
(45) Date of Patent: *Apr. 26, 2011

(54) 4-(4-TRIFLUOROMETHYL-3-THIO-BENZOYL)PYRAZOLES AND THEIR USE AS HERBICIDES

(75) Inventors: Hartmut Ahrens, Egelsbach (DE); Andreas van Almsick, Karben (DE); Monika Schmitt, Frankfurt (DE); Jan Dittgen, Frankfurt (DE); Martin Hills, Idstein (DE); Heinz Kehne, Hofheim (DE); Christopher Rosinger, Hofheim (DE); Stefan Lehr, Liederbach (DE); Dieter Feucht, Eschborn (DE)

(73) Assignee: Bayer Cropscience AG, Monheim (DE)

( * ) Notice: Subject to any disclaimer, the term of this patent is extended or adjusted under 35 U.S.C. 154(b) by 354 days.

This patent is subject to a terminal disclaimer.

(21) Appl. No.: 12/100,819

(22) Filed: Apr. 10, 2008

(65) Prior Publication Data

US 2009/0069184 A1  Mar. 12, 2009

(30) Foreign Application Priority Data

Apr. 12, 2007 (EP) .................................. 07007493

(51) Int. Cl.
A01N 43/56 (2006.01)
C07D 231/10 (2006.01)
A61P 13/00 (2006.01)

(52) U.S. Cl. ..................................... 504/282; 548/369.4
(58) Field of Classification Search .................. None
See application file for complete search history.

(56) References Cited

U.S. PATENT DOCUMENTS

| 4,261,729 A | 4/1981 | Konotsune et al. |
| 4,557,753 A | 12/1985 | Tanaka et al. |
| 4,687,858 A | 8/1987 | Konotsune et al. |
| 7,189,679 B2 | 3/2007 | Schmitt et al. |
| 2010/0004129 A1* | 1/2010 | Ahrens et al. ............... 504/282 |

FOREIGN PATENT DOCUMENTS

| EP | 0 203 428 A1 | 12/1986 |
| EP | 0 352 543 B1 | 9/1994 |
| WO | WO 00/03993 | 1/2000 |

OTHER PUBLICATIONS

Patani et al. (Chemical Reviews, 1996, vol. 96, 3147-3176).*

* cited by examiner

*Primary Examiner* — Kamal A Saeed
(74) *Attorney, Agent, or Firm* — Baker Donelson Bearman, Caldwell & Berkowitz, PC

(57) ABSTRACT

What is described are 4-(4-trifluoromethyl-3-thiobenzoyl) pyrazoles of the general formula (I) and their use as herbicides.

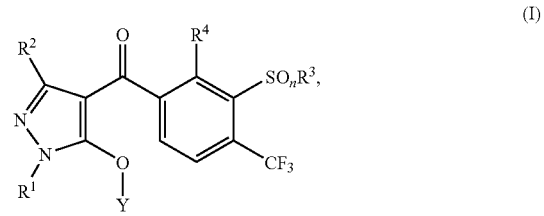

In this formula (I), $R^1$, $R^2$, $R^3$ and $R^4$ are radicals such as hydrogen and organic radicals, such as alkyl. Y is hydrogen or a protective group, such as tosyl.

20 Claims, No Drawings

4-(4-TRIFLUOROMETHYL-3-THIOBEN-ZOYL)PYRAZOLES AND THEIR USE AS HERBICIDES

CROSS REFERENCE TO RELATED APPLICATION

This application claims priority from EP 07 007 493.5 filed Apr. 12, 2007, the content of which is incorporated herein.

BACKGROUND OF THE INVENTION

1. Field of the Invention

The invention relates to the technical field of the herbicides, in particular that of the herbicides for the selective control of broad-leaved weeds and weed grasses in crops of useful plants.

2. Description of Related Art

From various publications, it is already known that certain benzoylpyrazoles have herbicidal properties. Thus, DE 2513750, EP 0 352 543, EP 0 203 428, WO 97/41106, WO 00/03993 and U.S. Pat. No. 4,557,753 mention benzoylpyrazoles substituted by various radicals.

However, the herbicidal activity of the compounds known from these publications is frequently insufficient. It is therefore an object of the present invention to provide herbicidally active compounds having herbicidal properties which are better than those of the compounds disclosed in the prior art.

SUMMARY OF THE INVENTION

It has now been found that certain 4-benzoylpyrazoles whose phenyl ring carries a thio group in the 3-position and a trifluoromethyl group in the 4-position are particularly suitable for use as herbicides. Part of the subject matter of the present invention are 4-(4-trifluoromethyl-3-thiobenzoyl)pyrazoles of the formula (I) or salts thereof

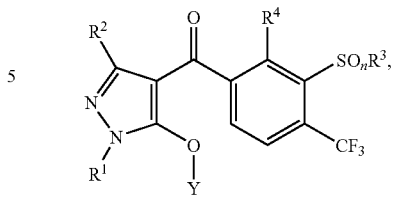

in which
$R^1$ is $(C_1-C_4)$-alkyl,
$R^2$ is hydrogen or $(C_1-C_4)$-alkyl,
$R^3$ is $(C_1-C_4)$-alkyl,
$R^4$ is $(C_1-C_4)$-alkyl,
Y is hydrogen, $(C_1-C_6)$-alkylsulfonyl, $(C_1-C_4)$-alkoxy-$(C_1-C_6)$-alkylsulfonyl, or is phenylsulfonyl, thiophenyl-2-sulfonyl, benzoyl, benzoyl-$(C_1-C_6)$-alkyl or benzyl, each of which is substituted by m identical or different radicals from the group consisting of halogen, $(C_1-C_4)$-alkyl and $(C_1-C_4)$-alkoxy,
m is 0, 1, 2 or 3,
n is 0, 1 or 2.

DETAILED DESCRIPTION OF A PREFERRED EMBODIMENT

Where Y is hydrogen, the compounds of the formula (I) according to the invention, depending on external conditions, such as solvent and pH, may occur in different tautomeric structures:

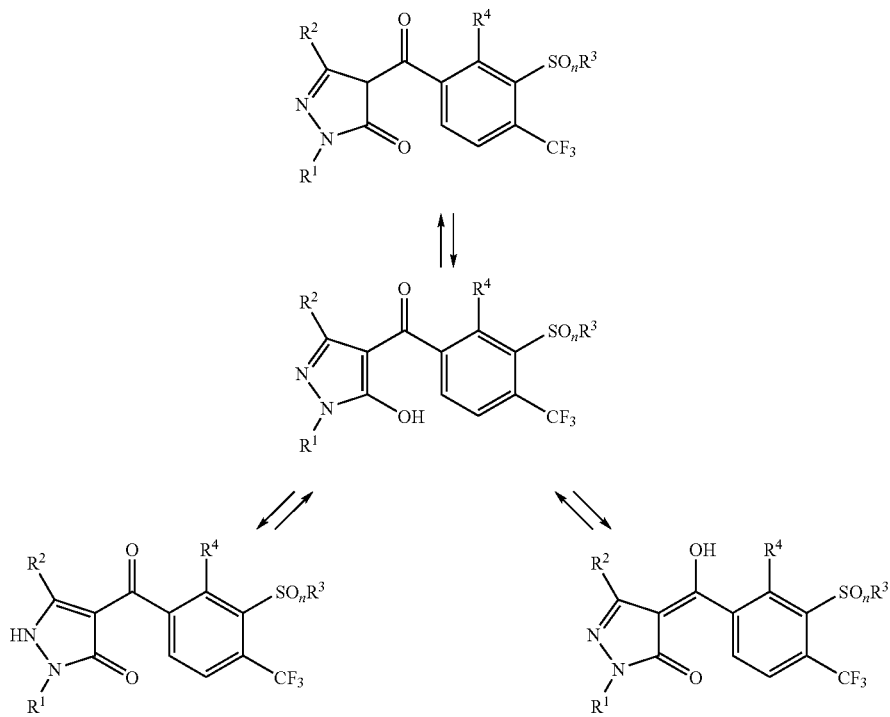

Depending on the nature of the substituents, the compounds of the general formula (I) contain an acidic proton which may be removed by reaction with a base. Suitable bases are, for example, hydrides, hydroxides and carbonates of lithium, sodium, potassium, magnesium and calcium, and also ammonia and organic amines, such as triethylamine and pyridine. It is also possible to form salts by forming adducts with organic acids, such as formic acid or acetic acid, and inorganic acids, such as phosphoric acid, hydrochloric acid or sulfuric acid. Such salts also form part of the subject matter of the invention.

In formula (I) and all subsequent formulae, alkyl radicals with more than two carbon atoms can be straight-chain or branched. Alkyl radicals are, for example, methyl, ethyl, n- or i-propyl, n-, i-, t- or 2-butyl, pentyls, hexyls, such as n-hexyl, i-hexyl and 1,3-dimethylbutyl. Halogen is fluorine, chlorine, bromine or iodine. Tosyl is 4-methylphenylsulfonyl.

If a group is polysubstituted by radicals, this is to be understood as meaning that this group is substituted by one or more identical or different of the radicals mentioned.

Depending on the type and the linkage of the substituents, the compounds of the general formula (I) can exist as stereoisomers. If, for example, one or more asymmetric carbon atoms or sulfur atoms (i.e. in the case of sulfoxides) are present, enantiomers and diastereomers may occur. Stereoisomers can be contained from the mixtures resulting from the preparation by means of customary separation methods, for example by chromatic separation methods. Likewise, stereoisomers may be prepared selectively by using stereoselective reactions employing optically active starting materials and/or auxiliaries. The invention also relates to all stereoisomers and their mixtures which are encompassed by the general formula (I), but not defined specifically.

Preference is given to compounds of the general formula (I) in which
$R^1$ is methyl or ethyl,
$R^2$ is hydrogen, methyl or ethyl,
$R^3$ is methyl or ethyl,
$R^4$ is methyl or ethyl,
Y is hydrogen, $(C_1-C_3)$-alkylsulfonyl, $(C_1-C_2)$-alkoxy-$(C_1-C_4)$-alkylsulfonyl, or is phenylsulfonyl, thiophenyl-2-sulfonyl, benzoyl, benzoyl-$(C_1-C_6)$-alkyl or benzyl, each of which is substituted by m methyl groups,
m is 0 or 1,
n is 0, 1 or 2.

Particular preference is given to compounds of the general formula (I) in which
$R^1$ is methyl or ethyl,
$R^2$ is hydrogen, methyl or ethyl,
$R^3$ is methyl or ethyl,
$R^4$ is methyl or ethyl,
Y is hydrogen,
n is 0, 1 or 2.

In all the formulae given below, the substituents and symbols have the same meaning as described under formula (I), unless defined otherwise.

Compounds according to the invention in which Y is hydrogen can be prepared, for example, by the process shown in scheme 1 and known from Acta Chem. Scand. 13, (1959), 1668-1670 by base-catalyzed reaction of a benzoyl halide (III) with a pyrazolone (II) or according to the process shown in scheme 2 and known, for example, from EP-A 0 186 117 by base-catalyzed reaction of a benzoyl halide (III) with a pyrazolone (II) and subsequent rearrangement.

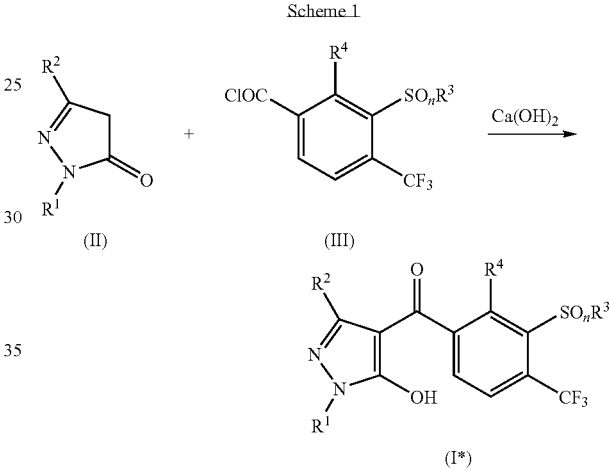

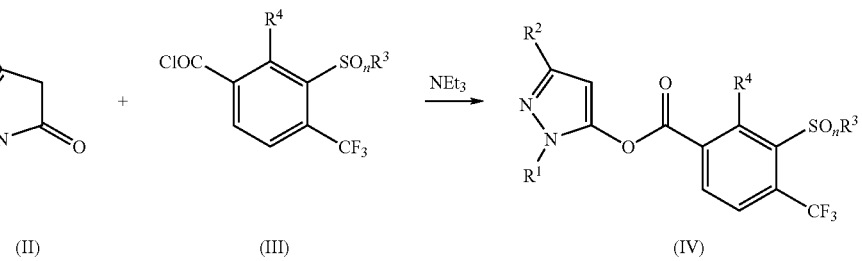

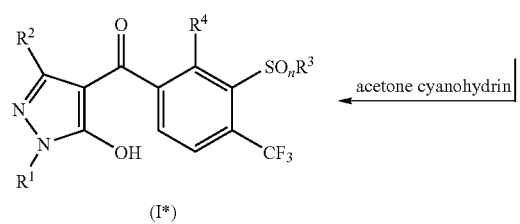

According to scheme 3, compounds according to the invention in which Y has a meaning different from hydrogen are expediently prepared from the compounds obtainable according to scheme 1 or 2, by base-catalyzed reaction with a suitable acylating agent Y—X of the formula (V) in which X is a leaving group, such as halogen. Such methods are known in principle to the person skilled in the art and described, for example, in DE-A 25 13 750.

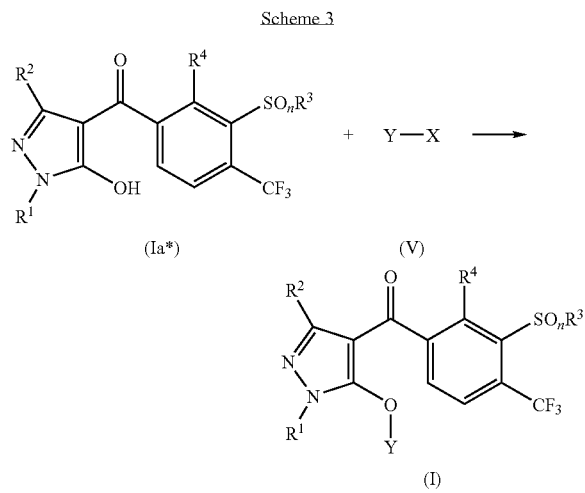

Compounds according to the invention can also be prepared according to the process shown in scheme 4 and known from WO 98/42678 by reacting a pyrazolone (II) with a halobenzoic acid (IIIa), subsequent nucleophilic aromatic substitution with a thio compound HS—R³ and, if appropriate, oxidation of the thio group. Here, L is, for example, chlorine, bromine, iodine or trifluoromethylsulfonyl. Such substitution reactions are known to the person skilled in the art and described, for example, in Houben-Weyl, Methoden der Organischen Chemie [Methods of organic chemistry], Georg Thieme Verlag Stuttgart, vol. E 11, additional and supplementary volumes to the fourth edition 1985, p. 174 et seq.

The compounds of the formula (III) mentioned above can be prepared, for example, from the compounds of the formula (IIIb) by reaction with acid chlorides according to methods known to the person skilled in the art.

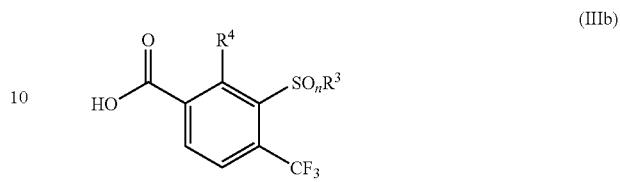

Compounds of the formulae (III) and (IIIb), in which R³, R⁴ and n are as defined for formula (I) are novel and also form part of the subject matter of the present application.

The starting materials used in the above schemes are either commercially available or can be prepared by methods known per se. Thus, the pyrazolones of the formula (II) can be prepared, for example, by the methods described in EP-A 0 240 001 and J. Prakt. Chem. 315, 382, (1973), and the benzoyl chlorides of the formula (III) can be prepared by the methods described in EP-A 0 527 036 and WO 03/014071.

The compounds of the formula (I) according to the invention have an excellent herbicidal activity against a broad range of economically important monocotyledonous and dicotyledonous harmful plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the peren-

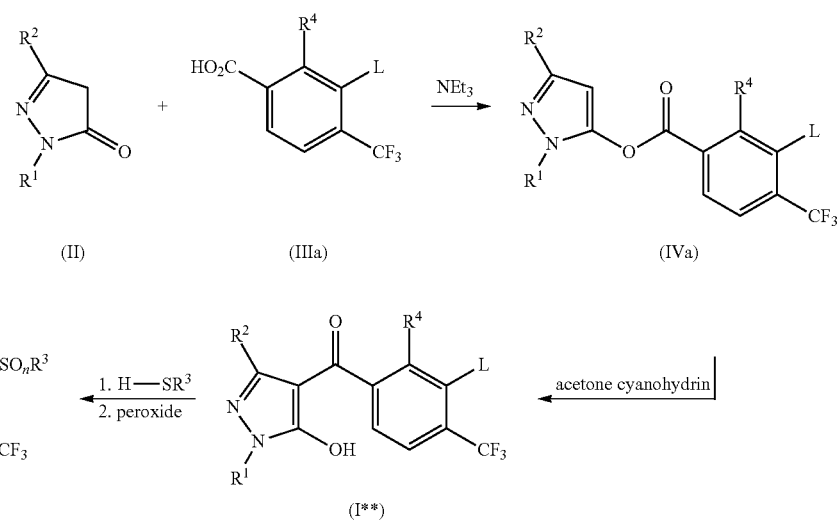

nial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennial weeds. Harmful plants which are found under the specific culture conditions of rice, such as, for example, *Echinochloa, Sagittaria, Alisma, Eleocharis, Scirpus* and *Cyperus* are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Apera spica venti, Chenopodium album, Lamium purpureum, Polygonum convulvulus, Stellaria media, Veronica hederifolia, Veronica persica* and *Viola tricolor.*

Although the compounds according to the invention have an outstanding herbicidal activity against monocotyledonous and dicotyledonous weeds, crop plants of economically important crops such as, for example, wheat, barley, rye, rice, corn, sugar beet, cotton and soybeans, only suffer negligible damage, if any. In particular, they are outstandingly well tolerated in cereals, such as wheat, barley and corn, in particular wheat. This is why the present compounds are highly suitable for the selective control of undesired vegetation in stands of agricultural useful plants or of ornamentals.

Owing to their herbicidal properties, the active substances can also be employed for controlling harmful plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassaya and corn, or else crops of sugar beet, cotton, soybeans, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid composition (WO 91/13972), A large number of techniques in molecular biology, with the aid of which novel transgenic plants with modified properties can be generated, are known in principle; see, for example, Sambrook et al., 1989, Molecular Cloning, A Laboratory Manual, $2^{nd}$ Ed., Cold Spring Harbor Laboratory Press, Cold Spring Harbor, N.Y.; or Winnacker "Gene und Klone" [Genes and Clones], VCH Weinheim $2^{nd}$ Edition 1996 or Christou, "Trends in Plant Science" 1 (1996) 423-431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or by expressing at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e. both monocotyledonous and dicotyledonous plants. Thus, transgenic plants can be obtained which exhibit modified properties owing to the overexpression, suppression or inhibition of homologous (=natural) genes or gene sequences or expression of heterologous (=foreign) genes or gene sequences.

When using the active substances according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water-based or oil-based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of adhesives, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57.

For further details on the formulation of crop protection agents see, for example G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441-445 (1986) or "The Pesticide Manual", 11th edition, The British Crop Protection Council and the Royal Soc. of Chemistry, 1997 and literature cited therein. Known herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number):
acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516H, i.e. 5-fluorine-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxy-dim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flucarbazoue; flufenacet; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; fluorochloridone; fluoroxypyr; flurtamone; fomesafen; foramsulfuron; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; iodosulfuron-methyl-sodium; isocarbamid; isopropalin; isoproturon; isouron; isoxaben; isoxapyrifop; karbutilate; lactofen; lenacil; linuron; MCPA; MCPB; mecoprop; mefenacet; mefluidid; mesosulfuron; mesotrione; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; pinoxaden; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propoxycarbazone; propyzamide; prosulfalin; prosulfocarb; prosulfuron (CGA-152005); prynachlor; pyrazolinate; pyrazon; pyrasulfotole; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy) phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; sulcotrione; sulfentrazon (FMC-97285, F-6285); sulfazuron; sulfometuron-methyl; sulfosate (ICI-A0224); TCA; tebutam (GCP-5544); tebuthiuron; tembotrione; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluoron; thiencarbazone; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023

For use, the formulations, which are present in commercially available form, are if appropriate diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use.

The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. Chemical Examples

Preparation of 1-ethyl-4-(3'-ethylsulfonyl-2'-methyl-4'-trifluoromethyl)benzoyl-5-hydroxypyrazole Step 1: 3-fluoro-2-methyl-4-trifluoromethylbenzoic acid 25.0 g (120.1 mmol) of 3-fluoro-4-trifluoromethylbenzoic acid were dissolved in 250 ml of THF, and 100.9 ml (2.5M in hexane, 252.3 mmol) of n-butyllithium were added dropwise at −40° C. The mixture was stirred for 3.5 h, and a solution of 51.2 g (360.4 mmol) of iodomethane in 50 ml of dry THF was then added dropwise. The mixture was stirred for 16 h, and after half an hour the temperature slowly increased to room temperature (RT). For work-up, 150 ml of 1M HCl were added carefully. The mixture was extracted with diethyl ether, and the organic phase was then extracted with 1M NaOH. The aqueous phase was acidified and then extracted with diethyl ether. The organic phase was washed with water, dried and freed from the solvent. The residue was titrated with n-heptane and the solid was removed by filtration. What was isolated were 13.5 g of the pure product.

Step 2: 3-ethylthio-2-methyl-4-trifluoromethylbenzoic acid 3.00 g (13.5 mmol) of 3-fluoro-2-methyl-4-trifluoromethylbenzoic acid were initially charged in 50 ml of N,N-dimethylformamide. 1.68 g (purity 60% by weight, 41.9 mmol) of NaH were added a little at a time. Towards the end of the evolution of gas, 1.77 g (purity 95% by weight, 27.0 mmol) of ethanethiol were added dropwise. The mixture was stirred at RT for 2 h and then heated at 80° C. for 10 h. The reaction mixture was cooled and, for workup, poured into ice-water and then acidified with concentrated hydrochloric acid. The product precipitated out and was separated off by filtration. What was isolated were 3.7 g of the pure product.

Step 3: Synthesis of 1-ethyl-4-(3'-ethylthio-2'-methyl-4'-trifluoromethyl)benzoyl-5-hydroxypyrazole 300 mg (1.14 mmol) of 3-ethylthio-2-methyl-4-trifluoromethylbenzoic acid were initially charged in 20 ml of dry $CH_2Cl_2$, and 288 mg (2.27 mmol) of oxalyl chloride were added. The mixture was heated at reflux for 15 min, after which no more evolution of gas could be observed. The content was cooled to RT and concentrated. The acid chloride obtained in this manner was dissolved in 20 ml of dry $CH_2Cl_2$, and the solution was added to a mixture of 140 mg (1.25 mmol) of 1-ethyl-5-hydroxypyrazole and catalytic amounts of 4-N,N-dimethylaminopyridine. 230 mg (2.27 mmol) of triethylamine were then slowly added dropwise, and the reaction mixture was stirred at RT for 16 h. For work-up, 3 ml of 1M HCl were added and, after phase separation, the organic phase was freed from the solvent. The enol ester obtained in this manner was taken up in 20 ml of acetonitrile, and 230 mg (2.27 mmol) of triethylamine were added. Eight drops of acetone cyanohydrin and a spatula tip of KCN were then added. The mixture was stirred at RT for 16 h and then concentrated. 20 ml of $CH_2Cl_2$ and then 3 ml of 1M HCl were added to the residue. After phase separation, the solvent was removed. The residue was purified by chromatography, which gave 182 mg of pure product.

Step 4: Synthesis of 1-ethyl-4-(3'-ethylsulfonyl-2'-methyl-4'-trifluoromethyl)benzoyl-5-hydroxypyrazole 182 mg (0.51 mmol) of 1-ethyl-4-(3'-ethylthio-2'-methyl-4'-trifluoromethyl)benzoyl-5-hydroxypyrazole were dissolved in 20 ml of $CH_2Cl_2$, and 376 mg (purity 70% by weight, 1.52 mmol) of meta-chloroperbenzoic acid were then added. The mixture was then stirred at RT for 16 h. For work-up, the mixture was diluted with $CH_2Cl_2$ and washed with 10% strength aqueous sodium hydrogensulfite solution. The mixture was acidified with 1M HCl, and, after phase separation and analytical confirmation of the absence of peroxides, the organic phase was dried and freed from the solvent. The residue was purified chromatographically, which gave 88.8 mg of pure product.

Preparation of 5-hydroxy-1,3-dimethyl-4-(2'-methyl-3'-methylsulfonyl-4'-trifluoromethyl)benzoylpyrazole Step 1: Synthesis of 2-methyl-3-methylthio-4-trifluoromethylbenzoic acid 300 mg (1.35 mmol) of 3-fluoro-2-methyl-4-trifluoromethylbenzoic acid were initially charged in 5 ml of N,N-dimethylformamide, and 59 mg (purity 60% by weight, 1.49 mmol) of NaH were added. The mixture was stirred for 10 min, and 199 mg (purity 95% by weight, 2.70 mmol) of sodium thiomethoxide were then added. The mixture was stirred at RT for 1.5 h and then heated at 80° C. for 16 h. The reaction mixture was cooled and, for workup, poured into water and extracted with ethyl acetate, and the aqueous phase was then acidified with concentrated HCl. The mixture was extracted twice with t-butyl methyl ether, dried and concentrated. This gave 310 mg of the product.

Step 2: Synthesis of 2-methyl-3-methylsulfonyl-4-trifluoromethylbenzoic acid 1.50 g (5.99 mmol) of 2-methyl-3-methylthio-4-trifluoromethylbenzoic acid were initially charged in 20 ml glacial acetic acid. 59 mg (0.18 mmol) of sodium tungstate (VI) dihydrate were added, and the mixture was then heated at 50-60° C. At this temperature, 2.45 ml (30% strength, 23.98 mmol) of an aqueous hydrogen peroxide solution were carefully added dropwise. The mixture was stirred at this temperature for a number of hours until HPLC analysis showed no more starting material and no more sulfoxide. The reaction mixture was then cooled and, for workup, poured into water. The mixture was extracted three times with ethyl acetate, the combined organic phases were washed with an aqueous saturated sodium hydrogen sulfite solution and, after analytical confirmation of the absence of peroxides, the mixture was acidified with 1M HCl. The organic phase was dried and freed from the solvents. What was isolated were 1.67 g of the pure product.

Step 3: Synthesis of 5-hydroxy-1,3-dimethyl-4-(2'-methyl-3'-methylsulfonyl-4'-trifluoromethyl)benzoylpyrazole 200 mg (0.71 mmol) of 2-methyl-3-methylsulfonyl-4-trifluoromethylbenzoic acid together with 87 mg (0.78 mmol) of 5-hydroxy-1,3-dimethylpyrazole and a catalytic amount of 4-N,N-dimethylaminopyridine were initially charged in 20 ml of dry $CH_2Cl_2$, and 163 mg (0.85 mmol) of 1-(3-dimethylaminopropyl)-3-ethylcarbodiimide hydrochloride were added. The mixture was stirred at RT for 3 h, and 3 ml of 1M HCl were then added. After phase separation, the aqueous phase was extracted with $CH_2Cl_2$. The organic phases were dried and concentrated. The residue was taken up in 20 ml of acetonitrile and 143 mg (1.42 mmol) of triethylamine, and eight drops of acetone cyanohydrine and a spatula tip of KCN were added. The mixture was stirred at RT for 16 h and concentrated. 15 ml of $CH_2Cl_2$ and then 2 ml of 1M HCl were added to the residue. After phase separation, the aqueous phase was extracted with $CH_2Cl_2$. The combined organic phases were dried and concentrated. The residue was purified chromatographically. What was isolated were 112.7 mg of pure product.

The examples given in the tables which follow were prepared analogously to the methods mentioned above, or can be obtained analogously to the methods mentioned above. These compounds are particularly preferred.

TABLE A

Compounds according to the invention of the formula (I) in which $R^1$ is methyl and $R^2$ and Y are each hydrogen

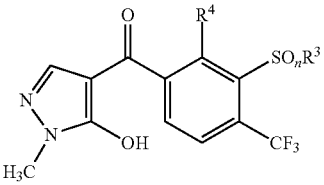

| No. | $R^3$ | $R^4$ | n | Physical data: $^1$H-NMR: δ [CDCl$_3$] |
|---|---|---|---|---|
| 1-1 | Me | Me | 0 | 7.68 (d, 1H), 7.45 (d, 1H), 7.30 (s, 1H), 3.71 (s, 3H), 2.68 (s, 3H), 2.31 (s, 3H) |
| 1-2 | Et | Me | 0 | 7.69 (d, 1H), 7.44 (d, 1H), 7.31 (s, 1H), 3.72 (s, 3H), 2.77 (q, 2H), 2.66 (s, 3H), 1.22 (t, 3H) |
| 1-3 | n-Pr | Me | 0 | |
| 1-4 | i-Pr | Me | 0 | |
| 1-5 | n-Bu | Me | 0 | |
| 1-6 | i-Bu | Me | 0 | |
| 1-7 | s-Bu | Me | 0 | |
| 1-8 | t-Bu | Me | 0 | |
| 1-9 | Me | Me | 1 | 7.71 (d, 1H), 7.56 (d, 1H), 7.28 (s, 1H), 3.72 (s, 3H), 3.03 (s, 3H), 2.90 (s, 3H) |
| 1-10 | Et | Me | 1 | 7.71 (d, 1H), 7.56 (d, 1H), 7.26 (s, 1H), 3.72 (s, 3H), 3.47 (dq, 1H), 2.96 (dq, 1H), 2.85 (s, 3H), 1.43 (t, 3H) |
| 1-11 | n-Pr | Me | 1 | |
| 1-12 | i-Pr | Me | 1 | |
| 1-13 | n-Bu | Me | 1 | |
| 1-14 | i-Bu | Me | 1 | |
| 1-15 | s-Bu | Me | 1 | |
| 1-16 | t-Bu | Me | 1 | |
| 1-17 | Me | Me | 2 | 7.91 (d, 1H), 7.67 (d, 1H), 7.27 (s, 1H), 3.72 (s, 3H), 3.27 (s, 3H), 2.76 (s, 3H) |
| 1-18 | Et | Me | 2 | |
| 1-19 | n-Pr | Me | 2 | |
| 1-20 | i-Pr | Me | 2 | |
| 1-21 | n-Bu | Me | 2 | |
| 1-22 | i-Bu | Me | 2 | |
| 1-23 | s-Bu | Me | 2 | |
| 1-24 | t-Bu | Me | 2 | |
| 1-25 | Me | Et | 0 | 7.68 (d, 1H), 7.42 (d, 1H), 7.30 (s, 1H), 3.71 (s, 3H), 3.16 (q, 2H), 2.36 (s, 3H), 1.19 (t, 3H) |
| 1-26 | Et | Et | 0 | |
| 1-27 | n-Pr | Et | 0 | |
| 1-28 | i-Pr | Et | 0 | |
| 1-29 | n-Bu | Et | 0 | |
| 1-30 | i-Bu | Et | 0 | |
| 1-31 | s-Bu | Et | 0 | |
| 1-32 | t-Bu | Et | 0 | |
| 1-33 | Me | Et | 1 | |
| 1-34 | Et | Et | 1 | |
| 1-35 | n-Pr | Et | 1 | |
| 1-36 | i-Pr | Et | 1 | |
| 1-37 | n-Bu | Et | 1 | |
| 1-38 | i-Bu | Et | 1 | |
| 1-39 | s-Bu | Et | 1 | |
| 1-40 | t-Bu | Et | 1 | |
| 1-41 | Me | Et | 2 | |
| 1-42 | Et | Et | 2 | |
| 1-43 | n-Pr | Et | 2 | |
| 1-44 | i-Pr | Et | 2 | |
| 1-45 | n-Bu | Et | 2 | |
| 1-46 | i-Bu | Et | 2 | |
| 1-47 | s-Bu | Et | 2 | |
| 1-48 | t-Bu | Et | 2 | |

The abbreviations used denote:
Bu = butyl  Et = ethyl  Me = methyl  Pr = propyl
i = iso  s = secondary  t = tertiary  Ph = phenyl

TABLE B

Compounds according to the invention of the formula (I) in which $R^1$ is ethyl and $R^2$ and Y are each hydrogen

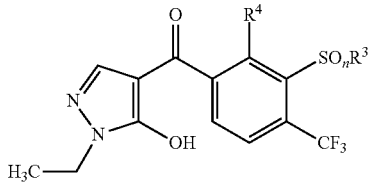

| No. | $R^3$ | $R^4$ | n | Physical data: $^1$H-NMR: δ [CDCl$_3$] |
|---|---|---|---|---|
| 2-1 | Me | Me | 0 | 7.69 (d, 1H), 7.47 (d, 1H), 7.31 (s, 1H), 4.08 (q, 2H), 2.69 (s, 3H), 2.31 (s, 3H), 1.46 (t, 3H) |
| 2-2 | Et | Me | 0 | 7.68 (d, 1H), 7.46 (d, 1H), 7.31 (s, 1H), 4.07 (q, 2H), 2.76 (q, 2H), 2.66 (s, 3H), 1.45 (t, 3H), 1.22 (t, 3H) |
| 2-3 | n-Pr | Me | 0 | |
| 2-4 | i-Pr | Me | 0 | |
| 2-5 | n-Bu | Me | 0 | |
| 2-6 | i-Bu | Me | 0 | |
| 2-7 | s-Bu | Me | 0 | |
| 2-8 | t-Bu | Me | 0 | |
| 2-9 | Me | Me | 1 | 7.71 (d, 1H), 7.57 (d, 1H), 7.29 (s, 1H), 4.09 (q, 2H), 3.03 (s, 3H), 2.90 (s, 3H), 1.46 (t, 3H) |
| 2-10 | Et | Me | 1 | 7.72 (d, 1H), 7.57 (d, 1H), 7.27 (s, 1H), 4.08 (q, 2H), 3.47 (dq, 1H), 2.96 (dq, 1H), 2.87 (s, 3H), 1.49–1.41 (m, 6H) |
| 2-11 | n-Pr | Me | 1 | |
| 2-12 | i-Pr | Me | 1 | |
| 2-13 | n-Bu | Me | 1 | |
| 2-14 | i-Bu | Me | 1 | |
| 2-15 | s-Bu | Me | 1 | |
| 2-16 | t-Bu | Me | 1 | |
| 2-17 | Me | Me | 2 | 7.91 (d, 1H), 7.67 (d, 1H), 7.28 (s, 1H), 4.08 (q, 2H), 3.27 (s, 3H), 2.78 (s, 3H), 1.46 (t, 3H) |
| 2-18 | Et | Me | 2 | 7.91 (d, 1H), 7.65 (d, 1H), 7.27 (s, 1H), 4.10 (q, 2H), 3.36 (q, 2H), 2.77 (s, 3H), 1.51–1.42 (m, 6H) |
| 2-19 | n-Pr | Me | 2 | |
| 2-20 | i-Pr | Me | 2 | |
| 2-21 | n-Bu | Me | 2 | |
| 2-22 | i-Bu | Me | 2 | |
| 2-23 | s-Bu | Me | 2 | |
| 2-24 | t-Bu | Me | 2 | |
| 2-25 | Me | Et | 0 | 7.69 (d, 1H), 7.45 (d, 1H), 7.30 (s, 1H), 4.08 (q, 2H), 3.16 (q, 2H), 2.36 (s, 3H), 1.46 (t, 3H), 1.20 (t, 3H) |
| 2-26 | Et | Et | 0 | |
| 2-27 | n-Pr | Et | 0 | |
| 2-28 | i-Pr | Et | 0 | |
| 2-29 | n-Bu | Et | 0 | |
| 2-30 | i-Bu | Et | 0 | |
| 2-31 | s-Bu | Et | 0 | |
| 2-32 | t-Bu | Et | 0 | |
| 2-33 | Me | Et | 1 | |
| 2-34 | Et | Et | 1 | |
| 2-35 | n-Pr | Et | 1 | |
| 2-36 | i-Pr | Et | 1 | |
| 2-37 | n-Bu | Et | 1 | |
| 2-38 | i-Bu | Et | 1 | |
| 2-39 | s-Bu | Et | 1 | |
| 2-40 | t-Bu | Et | 1 | |
| 2-41 | Me | Et | 2 | 7.90 (d, 1H), 7.65 (d, 1H), 7.28 (s, 1H), 4.10 (q, 2H), 3.32 (q, 2H), 3.29 (s, 3H), 1.46 (t, 3H), 1.23 (t, 3H) |
| 2-42 | Et | Et | 2 | |
| 2-43 | n-Pr | Et | 2 | |
| 2-44 | i-Pr | Et | 2 | |
| 2-45 | n-Bu | Et | 2 | |
| 2-46 | i-Bu | Et | 2 | |
| 2-47 | s-Bu | Et | 2 | |
| 2-48 | t-Bu | Et | 2 | |

TABLE C

Compounds according to the invention of the formula (I) in which $R^1$ and $R^2$ are each methyl and Y is hydrogen

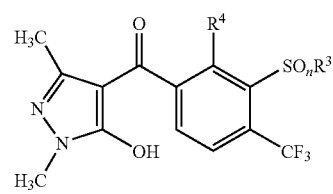

| No. | $R^3$ | $R^4$ | n | Physical data: $^1$H-NMR: δ [CDCl$_3$] |
|---|---|---|---|---|
| 3-1 | Me | Me | 0 | 7.69 (d, 1H), 7.29 (d, 1H), 3.62 (s, 3H), 2.60 (s, 3H), 2.29 (s, 3H), 1.62 (s, 3H) |
| 3-2 | Et | Me | 0 | 7.72 (d, 1H), 7.30 (d, 1H), 3.66 (s, 3H), 2.78 (q, 2H), 2.59 (s, 3H), 1.66 (s, 3H), 1.26 (t, 3H) |
| 3-3 | n-Pr | Me | 0 | |
| 3-4 | i-Pr | Me | 0 | |
| 3-5 | n-Bu | Me | 0 | |
| 3-6 | i-Bu | Me | 0 | |
| 3-7 | s-Bu | Me | 0 | |
| 3-8 | t-Bu | Me | 0 | |
| 3-9 | Me | Me | 1 | 7.72 (d, 1H), 7.42 (d, 1H), 3.66 (s, 3H), 3.01 (s, 3H), 2.82 (s, 3H), 1.69 (s, 3H) |
| 3-10 | Et | Me | 1 | 7.72 (d, 1H), 7.42 (d, 1H), 3.65 (s, 3H), 3.44 (dq, 1H), 2.93 (dq, 1H), 2.78 (s, 3H), 1.67 (s, 3H), 1.42 (t, 3H) |
| 3-11 | n-Pr | Me | 1 | |
| 3-12 | i-Pr | Me | 1 | |
| 3-13 | n-Bu | Me | 1 | |
| 3-14 | i-Bu | Me | 1 | |
| 3-15 | s-Bu | Me | 1 | |
| 3-16 | t-Bu | Me | 1 | |
| 3-17 | Me | Me | 2 | 7.91 (d, 1H), 7.53 (d, 1H), 3.65 (s, 3H), 3.23 (s, 3H), 2.71 (s, 3H), 1.68 (s, 3H) |
| 3-18 | Et | Me | 2 | |
| 3-19 | n-Pr | Me | 2 | |
| 3-20 | i-Pr | Me | 2 | |
| 3-21 | n-Bu | Me | 2 | |
| 3-22 | i-Bu | Me | 2 | |
| 3-23 | s-Bu | Me | 2 | |
| 3-24 | t-Bu | Me | 2 | |
| 3-25 | Me | Et | 0 | 7.70 (d, 1H), 7.28 (d, 1H), 3.63 (s, 3H), 3.42 (q, 2H), 2.32 s, 3H, 1.63 (s, 3H), 1.18 (t, 3H) |
| 3-26 | Et | Et | 0 | |
| 3-27 | n-Pr | Et | 0 | |
| 3-28 | i-Pr | Et | 0 | |
| 3-29 | n-Bu | Et | 0 | |
| 3-30 | i-Bu | Et | 0 | |
| 3-31 | s-Bu | Et | 0 | |
| 3-32 | t-Bu | Et | 0 | |
| 3-33 | Me | Et | 1 | |
| 3-34 | Et | Et | 1 | |
| 3-35 | n-Pr | Et | 1 | |
| 3-36 | i-Pr | Et | 1 | |
| 3-37 | n-Bu | Et | 1 | |
| 3-38 | i-Bu | Et | 1 | |
| 3-39 | s-Bu | Et | 1 | |
| 3-40 | t-Bu | Et | 1 | |
| 3-41 | Me | Et | 2 | |
| 3-42 | Et | Et | 2 | |
| 3-43 | n-Pr | Et | 2 | |
| 3-44 | i-Pr | Et | 2 | |
| 3-45 | n-Bu | Et | 2 | |
| 3-46 | i-Bu | Et | 2 | |
| 3-47 | s-Bu | Et | 2 | |
| 3-48 | t-Bu | Et | 2 | |

TABLE D

Compounds according to the invention of general formula (I)

[Structure: pyrazole bearing R¹ on N, R² on C3, C(=O) linkage to phenyl ring bearing R⁴, SO$_n$R³, CF₃ substituents, and O-Y on pyrazole C5]

| No. | R¹ | R² | R³ | R⁴ | n | Y | Physical data: ¹H-NMR: δ [CDCl₃] |
|---|---|---|---|---|---|---|---|
| 4-1 | Me | H | Me | Me | 0 | —SO₂-n-Pr | |
| 4-2 | Me | H | Et | Me | 0 | —SO₂-n-Pr | |
| 4-3 | Me | H | n-Pr | Me | 0 | —SO₂-n-Pr | |
| 4-4 | Me | H | Me | Me | 1 | —SO₂-n-Pr | 7.68 (d, 1H), 7.49 (d, 1H), 7.41 (s, 1H), 3.90 (s, 3H), 3.71 (m, 2H), 3.00 (s, 3H), 2.83 (s, 3H), 2.12 (m, 2H), 1.18 (t, 3H) |
| 4-5 | Me | H | Et | Me | 1 | —SO₂-n-Pr | |
| 4-6 | Me | H | n-Pr | Me | 1 | —SO₂-n-Pr | |
| 4-7 | Me | H | Me | Me | 2 | —SO₂-n-Pr | 7.90 (d, 1H), 7.62 (d, 1H), 7.43 (s, 1H), 3.91 (s, 3H), 3.67 (m, 2H), 3.26 (s, 3H), 2.71 (s, 3H), 2.11 (m, 2H), 1.18 (t, 3H) |
| 4-8 | Me | H | Et | Me | 2 | —SO₂-n-Pr | |
| 4-9 | Me | H | n-Pr | Me | 2 | —SO₂-n-Pr | |
| 4-10 | Me | H | Me | Me | 0 | —SO₂—(CH₂)₂OMe | |
| 4-11 | Me | H | Et | Me | 0 | —SO₂—(CH₂)₂OMe | |
| 4-12 | Me | H | n-Pr | Me | 0 | —SO₂—(CH₂)₂OMe | |
| 4-13 | Me | H | Me | Me | 1 | —SO₂—(CH₂)₂OMe | 7.68 (d, 1H), 7.48 (d, 1H), 7.41 (s, 1H), 4.04 (m, 4H), 3.91 (s, 3H), 3.46 (s, 3H) 3.01 (s, 3H), 2.83 (s, 3H) |
| 4-14 | Me | H | Et | Me | 1 | —SO₂—(CH₂)₂OMe | |
| 4-15 | Me | H | n-Pr | Me | 1 | —SO₂—(CH₂)₂OMe | |
| 4-16 | Me | H | Me | Me | 2 | —SO₂—(CH₂)₂OMe | 7.89 (d, 1H), 7.61 (d, 1H), 7.41 (s, 1H), 4.02 (m, 4H), 3.91 (s, 3H), 3.45 (s, 3H) 3.25 (s, 3H), 2.71 (s, 3H) |
| 4-17 | Me | H | Et | Me | 2 | —SO₂—(CH₂)₂OMe | |
| 4-18 | Me | H | n-Pr | Me | 2 | —SO₂—(CH₂)₂OMe | |
| 4-19 | Me | H | Me | Me | 0 | —SO₂-Ph | |
| 4-20 | Me | H | Et | Me | 0 | —SO₂-Ph | |
| 4-21 | Me | H | n-Pr | Me | 0 | —SO₂-Ph | |
| 4-22 | Me | H | Me | Me | 1 | —SO₂-Ph | 7.98 (d, 2H), 7.77 (tt, 1H), 7.62 (m, 3H), 7.52 (s, 1H), 7.37 (d, 1H), 3.78 (s, 3H), 2.98 (s, 3H), 2.77 (s, 3H) |
| 4-23 | Me | H | Et | Me | 1 | —SO₂-Ph | |
| 4-24 | Me | H | n-Pr | Me | 1 | —SO₂-Ph | |
| 4-25 | Me | H | Me | Me | 2 | —SO₂-Ph | 7.95 (d, 2H), 7.83-7.74 (m, 2H), 7.62 (m, 2H), 7.57 (s, 1H), 7.48 (d, 1H), 3.76 (s, 3H), 3.23 (s, 3H), 2.66 (s, 3H) |
| 4-26 | Me | H | Et | Me | 2 | —SO₂-Ph | |
| 4-27 | Me | H | n-Pr | Me | 2 | —SO₂-Ph | |
| 4-28 | Me | H | Me | Me | 0 | —SO₂-(4-Me-Ph) | |
| 4-29 | Me | H | Et | Me | 0 | —SO₂-(4-Me-Ph) | |
| 4-30 | Me | H | n-Pr | Me | 0 | —SO₂-(4-Me-Ph) | |
| 4-31 | Me | H | Me | Me | 1 | —SO₂-(4-Me-Ph) | 7.83 (d, 2H), 7.61 (d, 1H), 7.54 (s, 1H), 7.42-7.36 (m, 3H), 3.74 (s, 3H), 2.98 (s, 3H), 2.78 (s, 3H), 2.47 (s, 3H) |
| 4-32 | Me | H | Et | Me | 1 | —SO₂-(4-Me-Ph) | |
| 4-33 | Me | H | n-Pr | Me | 1 | —SO₂-(4-Me-Ph) | |

TABLE D-continued

Compounds according to the invention of general formula (I)

| No. | R¹ | R² | R³ | R⁴ | n | Y | Physical data: $^1$H-NMR: δ [CDCl$_3$] |
|---|---|---|---|---|---|---|---|
| 4-34 | Me | H | Me | Me | 2 | —SO$_2$-(4-Me-Ph) | 7.80 (m, 3H), 7.61 (s, 1H), 7.49 (m, 1H), 7.41 (d, 2H), 3.73 (s, 3H), 3.22 (s, 3H), 2.67 (s, 3H), 2.47 (s, 3H) |
| 4-35 | Me | H | Et | Me | 2 | —SO$_2$-(4-Me-Ph) | |
| 4-36 | Me | H | n-Pr | Me | 2 | —SO$_2$-(4-Me-Ph) | |
| 4-37 | Me | H | Me | Me | 0 | —SO$_2$-(thien-2-yl) | |
| 4-38 | Me | H | Et | Me | 0 | —SO$_2$-(thien-2-yl) | |
| 4-39 | Me | H | n-Pr | Me | 0 | —SO$_2$-(thien-2-yl) | |
| 4-40 | Me | H | Me | Me | 1 | —SO$_2$-(thien-2-yl) | 7.86 (m, 2H), 7.62 (d, 1H), 7.53 (s, 1H), 7.39 (d, 1H), 7.22 (dd, 1H), 3.79 (s, 3H), 2.98 (s, 3H), 2.78 (s, 3H) |
| 4-41 | Me | H | Et | Me | 1 | —SO$_2$-(Thien-2-yl) | |
| 4-42 | Me | H | n-Pr | Me | 1 | —SO$_2$-(Thien-2-yl) | |
| 4-43 | Me | H | Me | Me | 2 | —SO$_2$-(Thien-2-yl) | 7.88 (d, 1H), 7.86-7.82 (m, 2H), 7.58 (s, 1H), 7.52 (m, 1H), 7.22 (m, 1H), 3.77 (s, 3H), 3.22 (s, 3H), 2.67 (s, 3H) |
| 4-44 | Me | H | Et | Me | 2 | —SO$_2$-(Thien-2-yl) | |
| 4-45 | Me | H | n-Pr | Me | 2 | —SO$_2$-(Thien-2-yl) | |
| 4-46 | Me | H | Me | Me | 0 | —CO-Ph | |
| 4-47 | Me | H | Et | Me | 0 | —CO-Ph | |
| 4-48 | Me | H | n-Pr | Me | 0 | —CO-Ph | |
| 4-49 | Me | H | Me | Me | 1 | —CO-Ph | 7.93-7.87 (m, 3H), 7.68 (t, 1H), 7.52-7.36 (m, 4H), 3.73 (s, 3H), 2.87 (s, 3H), 2.81 (s, 3H) |
| 4-50 | Me | H | Et | Me | 1 | —CO-Ph | |
| 4-51 | Me | H | n-Pr | Me | 1 | —CO-Ph | |
| 4-52 | Me | H | Me | Me | 2 | —CO-Ph | 7.93 (s, 1H), 7.85 (d, 2H), 7.68 (tt, 1H), 7.62 (d, 1H), 7.52-7.46 (m, 3H), 3.74 (s, 3H), 3.10 (s, 3H), 2.68 (s, 3H) |
| 4-53 | Me | H | Et | Me | 2 | —CO-Ph | |
| 4-54 | Me | H | n-Pr | Me | 2 | —CO-Ph | |
| 4-55 | Me | H | Me | Me | 0 | —CO-SEt | |
| 4-56 | Me | H | Et | Me | 0 | —CO-SEt | |
| 4-57 | Me | H | n-Pr | Me | 0 | —CO-SEt | |
| 4-58 | Me | H | Me | Me | 1 | —CO-SEt | 7.72 (s, 1H), 7.67 (d, 1H), 7.42 (d, 1H), 3.72 (s, 3H), 2.99 (s, 3H), 2.92 (q, 2H), 2.81 (s, 3H), 1.32 (t, 3H) |
| 4-59 | Me | H | Et | Me | 1 | —CO-SEt | |
| 4-60 | Me | H | n-Pr | Me | 1 | —CO-SEt | |
| 4-61 | Me | H | Me | Me | 2 | —CO-SEt | 7.87 (d, 1H), 7.78 (s, 1H), 7.53 (d, 1H), 3.72 (s, 3H), 3.22 (s, 3H), 2.89 (q, 2H), 2.68 (s, 3H), 1.32 (t, 3H) |
| 4-62 | Me | H | Et | Me | 2 | —CO-SEt | |
| 4-63 | Me | H | n-Pr | Me | 2 | —CO-SEt | |
| 4-64 | Me | H | Me | Me | 0 | —CH$_2$—CO-(4-Me-Ph) | |
| 4-65 | Me | H | Et | Me | 0 | —CH$_2$—CO-(4-Me-Ph) | |
| 4-66 | Me | H | n-Pr | Me | 0 | —CH$_2$—CO-(4-Me-Ph) | |

TABLE D-continued

Compounds according to the invention of general formula (I)

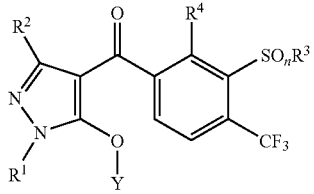

| No. | R$^1$ | R$^2$ | R$^3$ | R$^4$ | n | Y | Physical data: $^1$H-NMR: δ [CDCl$_3$] |
|---|---|---|---|---|---|---|---|
| 4-67 | Me | H | Me | Me | 1 | —CH$_2$—CO-(4-Me-Ph) | 7.82 (d, 2H), 7.62 (d, 1H), 7.39 (d, 1H), 7.29 (d, 2H), 7.13 (s, 1H), 6.22 (d, 1H), 6.12 (d, 1H), 3.89 (s, 3H), 2.96 (s, 3H), 2.72 (s, 3H), 2.41 (s, 3H) |
| 4-68 | Me | H | Et | Me | 1 | —CH$_2$—CO-(4-Me-Ph) | |
| 4-69 | Me | H | n-Pr | Me | 1 | —CH$_2$—CO-(4-Me-Ph) | |
| 4-70 | Me | H | Me | Me | 2 | —CH$_2$—CO-(4-Me-Ph) | 7.82 (m, 3H), 7.52 (d, 1H), 7.30 (d, 2H), 7.12 (s, 1H), 6.16 (s, 2H), 3.90 (s, 3H), 3.21 (s, 3H), 2.58 (s, 3H), 2.42 (s, 3H) |
| 4-71 | Me | H | Et | Me | 2 | —CH$_2$—CO-(4-Me-Ph) | |
| 4-72 | Me | H | n-Pr | Me | 2 | —CH$_2$—CO-(4-Me-Ph) | |
| 4-73 | Et | H | Me | Me | 0 | —SO$_2$-n-Pr | |
| 4-74 | Et | H | Et | Me | 0 | —SO$_2$-n-Pr | |
| 4-75 | Et | H | n-Pr | Me | 0 | —SO$_2$-n-Pr | |
| 4-76 | Et | H | Me | Me | 1 | —SO$_2$-n-Pr | |
| 4-77 | Et | H | Et | Me | 1 | —SO$_2$-n-Pr | |
| 4-78 | Et | H | n-Pr | Me | 1 | —SO$_2$-n-Pr | |
| 4-79 | Et | H | Me | Me | 2 | —SO$_2$-n-Pr | |
| 4-80 | Et | H | Et | Me | 2 | —SO$_2$-n-Pr | |
| 4-81 | Et | H | n-Pr | Me | 2 | —SO$_2$-n-Pr | |
| 4-82 | Et | H | Me | Me | 0 | —SO$_2$—(CH$_2$)$_2$OMe | |
| 4-83 | Et | H | Et | Me | 0 | —SO$_2$—(CH$_2$)$_2$OMe | |
| 4-84 | Et | H | n-Pr | Me | 0 | —SO$_2$—(CH$_2$)$_2$OMe | |
| 4-85 | Et | H | Me | Me | 1 | —SO$_2$—(CH$_2$)$_2$OMe | |
| 4-86 | Et | H | Et | Me | 1 | —SO$_2$—(CH$_2$)$_2$OMe | |
| 4-87 | Et | H | n-Pr | Me | 1 | —SO$_2$—(CH$_2$)$_2$OMe | |
| 4-88 | Et | H | Me | Me | 2 | —SO$_2$—(CH$_2$)$_2$OMe | |
| 4-89 | Et | H | Et | Me | 2 | —SO$_2$—(CH$_2$)$_2$OMe | |
| 4-90 | Et | H | n-Pr | Me | 2 | —SO$_2$—(CH$_2$)$_2$OMe | |
| 4-91 | Et | H | Me | Me | 0 | —SO$_2$-Ph | |
| 4-92 | Et | H | Et | Me | 0 | —SO$_2$-Ph | |
| 4-93 | Et | H | n-Pr | Me | 0 | —SO$_2$-Ph | |
| 4-94 | Et | H | Me | Me | 1 | —SO$_2$-Ph | |
| 4-95 | Et | H | Et | Me | 1 | —SO$_2$-Ph | |
| 4-96 | Et | H | n-Pr | Me | 1 | —SO$_2$-Ph | |
| 4-97 | Et | H | Me | Me | 2 | —SO$_2$-Ph | |
| 4-98 | Et | H | Et | Me | 2 | —SO$_2$-Ph | |
| 4-99 | Et | H | n-Pr | Me | 2 | —SO$_2$-Ph | |
| 4-100 | Et | H | Me | Me | 0 | —SO$_2$-(4-Me-Ph) | |
| 4-101 | Et | H | Et | Me | 0 | —SO$_2$-(4-Me-Ph) | |
| 4-102 | Et | H | n-Pr | Me | 0 | —SO$_2$-(4-Me-Ph) | |
| 4-103 | Et | H | Me | Me | 1 | —SO$_2$-(4-Me-Ph) | |
| 4-104 | Et | H | Et | Me | 1 | —SO$_2$-(4-Me-Ph) | |
| 4-105 | Et | H | n-Pr | Me | 1 | —SO$_2$-(4-Me-Ph) | |
| 4-106 | Et | H | Me | Me | 2 | —SO$_2$-(4-Me-Ph) | |
| 4-107 | Et | H | Et | Me | 2 | —SO$_2$-(4-Me-Ph) | |
| 4-108 | Et | H | n-Pr | Me | 2 | —SO$_2$-(4-Me-Ph) | |
| 4-109 | Et | H | Me | Me | 0 | —SO$_2$-(thien-2-yl) | |
| 4-110 | Et | H | Et | Me | 0 | —SO$_2$-(thien-2-yl) | |
| 4-111 | Et | H | n-Pr | Me | 0 | —SO$_2$-(thien-2-yl) | |
| 4-112 | Et | H | Me | Me | 1 | —SO$_2$-(thien-2-yl) | |
| 4-113 | Et | H | Et | Me | 1 | —SO$_2$-(thien-2-yl) | |
| 4-114 | Et | H | n-Pr | Me | 1 | —SO$_2$-(thien-2-yl) | |
| 4-115 | Et | H | Me | Me | 2 | —SO$_2$-(thien-2-yl) | |
| 4-116 | Et | H | Et | Me | 2 | —SO$_2$-(thien-2-yl) | |
| 4-117 | Et | H | n-Pr | Me | 2 | —SO$_2$-(thien-2-yl) | |
| 4-118 | Et | H | Me | Me | 0 | —CO-Ph | |
| 4-119 | Et | H | Et | Me | 0 | —CO-Ph | |

TABLE D-continued

Compounds according to the invention of general formula (I)

| No. | R$^1$ | R$^2$ | R$^3$ | R$^4$ | n | Y | Physical data: $^1$H-NMR: δ [CDCl$_3$] |
|---|---|---|---|---|---|---|---|
| 4-120 | Et | H | n-Pr | Me | 0 | —CO-Ph | |
| 4-121 | Et | H | Me | Me | 1 | —CO-Ph | |
| 4-122 | Et | H | Et | Me | 1 | —CO-Ph | |
| 4-123 | Et | H | n-Pr | Me | 1 | —CO-Ph | |
| 4-124 | Et | H | Me | Me | 2 | —CO-Ph | |
| 4-125 | Et | H | Et | Me | 2 | —CO-Ph | |
| 4-126 | Et | H | n-Pr | Me | 2 | —CO-Ph | |
| 4-127 | Et | H | Me | Me | 0 | —CO-SEt | |
| 4-128 | Et | H | Et | Me | 0 | —CO-SEt | |
| 4-129 | Et | H | n-Pr | Me | 0 | —CO-SEt | |
| 4-130 | Et | H | Me | Me | 1 | —CO-SEt | |
| 4-131 | Et | H | Et | Me | 1 | —CO-SEt | |
| 4-132 | Et | H | n-Pr | Me | 1 | —CO-SEt | |
| 4-133 | Et | H | Me | Me | 2 | —CO-SEt | |
| 4-134 | Et | H | Et | Me | 2 | —CO-SEt | |
| 4-135 | Et | H | n-Pr | Me | 2 | —CO-SEt | |
| 4-136 | Et | H | Me | Me | 0 | —CH$_2$—CO-(4-Me-Ph) | |
| 4-137 | Et | H | Et | Me | 0 | —CH$_2$—CO-(4-Me-Ph) | |
| 4-138 | Et | H | n-Pr | Me | 0 | —CH$_2$—CO-(4-Me-Ph) | |
| 4-139 | Et | H | Me | Me | 1 | —CH$_2$—CO-(4-Me-Ph) | |
| 4-140 | Et | H | Et | Me | 1 | —CH$_2$—CO-(4-Me-Ph) | |
| 4-141 | Et | H | n-Pr | Me | 1 | —CH$_2$—CO-(4-Me-Ph) | |
| 4-142 | Et | H | Me | Me | 2 | —CH$_2$—CO-(4-Me-Ph) | |
| 4-143 | Et | H | Et | Me | 2 | —CH$_2$—CO-(4-Me-Ph) | |
| 4-144 | Et | H | n-Pr | Me | 2 | —CH$_2$—CO-(4-Me-Ph) | |
| 4-145 | Me | Me | Me | Me | 0 | —SO$_2$-n-Pr | |
| 4-146 | Me | Me | Et | Me | 0 | —SO$_2$-n-Pr | |
| 4-147 | Me | Me | n-Pr | Me | 0 | —SO$_2$-n-Pr | |
| 4-148 | Me | Me | Me | Me | 1 | —SO$_2$-n-Pr | |
| 4-149 | Me | Me | Et | Me | 1 | —SO$_2$-n-Pr | |
| 4-150 | Me | Me | n-Pr | Me | 1 | —SO$_2$-n-Pr | |
| 4-151 | Me | Me | Me | Me | 2 | —SO$_2$-n-Pr | |
| 4-152 | Me | Me | Et | Me | 2 | —SO$_2$-n-Pr | |
| 4-153 | Me | Me | n-Pr | Me | 2 | —SO$_2$-n-Pr | |
| 4-154 | Me | Me | Me | Me | 0 | —SO$_2$—(CH$_2$)$_2$OMe | |
| 4-155 | Me | Me | Et | Me | 0 | —SO$_2$—(CH$_2$)$_2$OMe | |
| 4-156 | Me | Me | n-Pr | Me | 0 | —SO$_2$—(CH$_2$)$_2$OMe | |
| 4-157 | Me | Me | Me | Me | 1 | —SO$_2$—(CH$_2$)$_2$OMe | |
| 4-158 | Me | Me | Et | Me | 1 | —SO$_2$—(CH$_2$)$_2$OMe | |
| 4-159 | Me | Me | n-Pr | Me | 1 | —SO$_2$—(CH$_2$)$_2$OMe | |
| 4-160 | Me | Me | Me | Me | 2 | —SO$_2$—(CH$_2$)$_2$OMe | |
| 4-161 | Me | Me | Et | Me | 2 | —SO$_2$—(CH$_2$)$_2$OMe | |
| 4-162 | Me | Me | n-Pr | Me | 2 | —SO$_2$—(CH$_2$)$_2$OMe | |
| 4-163 | Me | Me | Me | Me | 0 | —SO$_2$-Ph | |
| 4-164 | Me | Me | Et | Me | 0 | —SO$_2$-Ph | |
| 4-165 | Me | Me | n-Pr | Me | 0 | —SO$_2$-Ph | |
| 4-166 | Me | Me | Me | Me | 1 | —SO$_2$-Ph | |
| 4-167 | Me | Me | Et | Me | 1 | —SO$_2$-Ph | |
| 4-168 | Me | Me | n-Pr | Me | 1 | —SO$_2$-Ph | |
| 4-169 | Me | Me | Me | Me | 2 | —SO$_2$-Ph | |
| 4-170 | Me | Me | Et | Me | 2 | —SO$_2$-Ph | |
| 4-171 | Me | Me | n-Pr | Me | 2 | —SO$_2$-Ph | |
| 4-172 | Me | Me | Me | Me | 0 | —SO$_2$-(4-Me-Ph) | |
| 4-173 | Me | Me | Et | Me | 0 | —SO$_2$-(4-Me-Ph) | |
| 4-174 | Me | Me | n-Pr | Me | 0 | —SO$_2$-(4-Me-Ph) | |
| 4-175 | Me | Me | Me | Me | 1 | —SO$_2$-(4-Me-Ph) | |
| 4-176 | Me | Me | Et | Me | 1 | —SO$_2$-(4-Me-Ph) | |
| 4-177 | Me | Me | n-Pr | Me | 1 | —SO$_2$-(4-Me-Ph) | |
| 4-178 | Me | Me | Me | Me | 2 | —SO$_2$-(4-Me-Ph) | |
| 4-179 | Me | Me | Et | Me | 2 | —SO$_2$-(4-Me-Ph) | |
| 4-180 | Me | Me | n-Pr | Me | 2 | —SO$_2$-(4-Me-Ph) | |
| 4-181 | Me | Me | Me | Me | 0 | —SO$_2$-(thien-2-yl) | |
| 4-182 | Me | Me | Et | Me | 0 | —SO$_2$-(thien-2-yl) | |
| 4-183 | Me | Me | n-Pr | Me | 0 | —SO$_2$-(thien-2-yl) | |

TABLE D-continued

Compounds according to the invention of general formula (I)

| No. | R¹ | R² | R³ | R⁴ | n | Y | Physical data: $^1$H-NMR: δ [CDCl$_3$] |
|---|---|---|---|---|---|---|---|
| 4-184 | Me | Me | Me | Me | 1 | —SO$_2$-(thien-2-yl) | |
| 4-185 | Me | Me | Et | Me | 1 | —SO$_2$-(thien-2-yl) | |
| 4-186 | Me | Me | n-Pr | Me | 1 | —SO$_2$-(thien-2-yl) | |
| 4-187 | Me | Me | Me | Me | 2 | —SO$_2$-(thien-2-yl) | |
| 4-188 | Me | Me | Et | Me | 2 | —SO$_2$-(thien-2-yl) | |
| 4-189 | Me | Me | n-Pr | Me | 2 | —SO$_2$-(thien-2-yl) | |
| 4-190 | Me | Me | Me | Me | 0 | —CO-Ph | |
| 4-191 | Me | Me | Et | Me | 0 | —CO-Ph | |
| 4-192 | Me | Me | n-Pr | Me | 0 | —CO-Ph | |
| 4-193 | Me | Me | Me | Me | 1 | —CO-Ph | |
| 4-194 | Me | Me | Et | Me | 1 | —CO-Ph | |
| 4-195 | Me | Me | n-Pr | Me | 1 | —CO-Ph | |
| 4-196 | Me | Me | Me | Me | 2 | —CO-Ph | |
| 4-197 | Me | Me | Et | Me | 2 | —CO-Ph | |
| 4-198 | Me | Me | n-Pr | Me | 2 | —CO-Ph | |
| 4-199 | Me | Me | Me | Me | 0 | —CO-SEt | |
| 4-200 | Me | Me | Et | Me | 0 | —CO-SEt | |
| 4-201 | Me | Me | n-Pr | Me | 0 | —CO-SEt | |
| 4-202 | Me | Me | Me | Me | 1 | —CO-SEt | |
| 4-203 | Me | Me | Et | Me | 1 | —CO-SEt | |
| 4-204 | Me | Me | n-Pr | Me | 1 | —CO-SEt | |
| 4-205 | Me | Me | Me | Me | 2 | —CO-SEt | |
| 4-206 | Me | Me | Et | Me | 2 | —CO-SEt | |
| 4-207 | Me | Me | n-Pr | Me | 2 | —CO-SEt | |
| 4-208 | Me | Me | Me | Me | 0 | —CH$_2$—CO-(4-Me-Ph) | |
| 4-209 | Me | Me | Et | Me | 0 | —CH$_2$—CO-(4-Me-Ph) | |
| 4-210 | Me | Me | n-Pr | Me | 0 | —CH$_2$—CO-(4-Me-Ph) | |
| 4-211 | Me | Me | Me | Me | 1 | —CH$_2$—CO-(4-Me-Ph) | |
| 4-212 | Me | Me | Et | Me | 1 | —CH$_2$—CO-(4-Me-Ph) | |
| 4-213 | Me | Me | n-Pr | Me | 1 | —CH$_2$—CO-(4-Me-Ph) | |
| 4-214 | Me | Me | Me | Me | 2 | —CH$_2$—CO-(4-Me-Ph) | |
| 4-215 | Me | Me | Et | Me | 2 | —CH$_2$—CO-(4-Me-Ph) | |
| 4-216 | Me | Me | n-Pr | Me | 2 | —CH$_2$—CO-(4-Me-Ph) | |

TABLE E

Compounds according to the invention of general formula (IIIb)

| No. | R³ | R⁴ | n | Physical data: $^1$H-NMR: δ [CDCl$_3$] |
|---|---|---|---|---|
| 5-1 | Me | Me | 0 | 7.98 (d, 1H), 7.66 (d, 1H), 2.92 (s, 3H), 2.28 (s, 3H) |
| 5-2 | Et | Me | 0 | 7.98 (d, 1H), 7.67 (d, 1H), 2.91 (s, 3H), 2.75 (q, 2H), 1.22 (t, 3H) |
| 5-3 | n-Pr | Me | 0 | |
| 5-4 | i-Pr | Me | 0 | |
| 5-5 | n-Bu | Me | 0 | |
| 5-6 | i-Bu | Me | 0 | |
| 5-7 | s-Bu | Me | 0 | |
| 5-8 | t-Bu | Me | 0 | |
| 5-9 | Me | Me | 1 | (DMSO-d$_6$): 7.92 (d, 1H), 7.81 (d, 1H), 3.04 (s, 3H), 2.91 (s, 3H) |
| 5-10 | Et | Me | 1 | (DMSO-d$_6$): 7.92 (d, 1H), 7.82 (d, 1H), 3.46 (dq, 1H), 3.02 (dq, 1H), 2.88 (s, 3H), 1.27 (t, 3H) |
| 5-11 | n-Pr | Me | 1 | |
| 5-12 | i-Pr | Me | 1 | |
| 5-13 | n-Bu | Me | 1 | |
| 5-14 | i-Bu | Me | 1 | |
| 5-15 | s-Bu | Me | 1 | |
| 5-16 | t-Bu | Me | 1 | |
| 5-17 | Me | Me | 2 | 8.11 (d, 1H), 7.87 (d, 1H), 3.30 (s, 3H), 2.96 (s, 3H) |
| 5-18 | Et | Me | 2 | |
| 5-19 | n-Pr | Me | 2 | |

TABLE E-continued

Compounds according to the invention of general formula (IIIb)

$$\text{HO-C(=O)-C}_6\text{H}_2(\text{R}^4)(\text{SO}_n\text{R}^3)(\text{CF}_3)$$

| No. | $R^3$ | $R^4$ | n | Physical data: $^1$H-NMR: δ [CDCl$_3$] |
|---|---|---|---|---|
| 5-20 | i-Pr | Me | 2 | |
| 5-21 | n-Bu | Me | 2 | |
| 5-22 | i-Bu | Me | 2 | |
| 5-23 | s-Bu | Me | 2 | |
| 5-24 | t-Bu | Me | 2 | |
| 5-25 | Me | Et | 0 | |
| 5-26 | Et | Et | 0 | |
| 5-27 | n-Pr | Et | 0 | |
| 5-28 | i-Pr | Et | 0 | |
| 5-29 | n-Bu | Et | 0 | |
| 5-30 | i-Bu | Et | 0 | |
| 5-31 | s-Bu | Et | 0 | |
| 5-32 | t-Bu | Et | 0 | |
| 5-33 | Me | Et | 1 | |
| 5-34 | Et | Et | 1 | |
| 5-35 | n-Pr | Et | 1 | |
| 5-36 | i-Pr | Et | 1 | |
| 5-37 | n-Bu | Et | 1 | |
| 5-38 | i-Bu | Et | 1 | |
| 5-39 | s-Bu | Et | 1 | |
| 5-40 | t-Bu | Et | 1 | |
| 5-41 | Me | Et | 2 | 8.07 (d, 1H), 7.87 (d, 1H), 3.50 (q, 2H), 3.29 (s, 3H), 1.36 (t, 3H) |
| 5-42 | Et | Et | 2 | |
| 5-43 | n-Pr | Et | 2 | |
| 5-44 | i-Pr | Et | 2 | |
| 5-45 | n-Bu | Et | 2 | |
| 5-46 | i-Bu | Et | 2 | |
| 5-47 | s-Bu | Et | 2 | |
| 5-48 | t-Bu | Et | 2 | |

TABLE F

Compounds according to the invention of general formula (III)

$$\text{Cl-C(=O)-C}_6\text{H}_2(\text{R}^4)(\text{SO}_n\text{R}^3)(\text{CF}_3)$$

| No. | $R^3$ | $R^4$ | n | Physical data: $^1$H-NMR: δ [CDCl$_3$] |
|---|---|---|---|---|
| 6-1 | Me | Me | 0 | |
| 6-2 | Et | Me | 0 | |
| 6-3 | n-Pr | Me | 0 | |
| 6-4 | i-Pr | Me | 0 | |
| 6-5 | n-Bu | Me | 0 | |
| 6-6 | i-Bu | Me | 0 | |
| 6-7 | s-Bu | Me | 0 | |
| 6-8 | t-Bu | Me | 0 | |
| 6-9 | Me | Me | 1 | |
| 6-10 | Et | Me | 1 | |
| 6-11 | n-Pr | Me | 1 | |
| 6-12 | i-Pr | Me | 1 | |
| 6-13 | n-Bu | Me | 1 | |
| 6-14 | i-Bu | Me | 1 | |
| 6-15 | s-Bu | Me | 1 | |
| 6-16 | t-Bu | Me | 1 | |
| 6-17 | Me | Me | 2 | |
| 6-18 | Et | Me | 2 | |
| 6-19 | n-Pr | Me | 2 | |
| 6-20 | i-Pr | Me | 2 | |
| 6-21 | n-Bu | Me | 2 | |
| 6-22 | i-Bu | Me | 2 | |
| 6-23 | s-Bu | Me | 2 | |
| 6-24 | t-Bu | Me | 2 | |
| 6-25 | Me | Et | 0 | |
| 6-26 | Et | Et | 0 | |
| 6-27 | n-Pr | Et | 0 | |
| 6-28 | i-Pr | Et | 0 | |
| 6-29 | n-Bu | Et | 0 | |
| 6-30 | i-Bu | Et | 0 | |
| 6-31 | s-Bu | Et | 0 | |
| 6-32 | t-Bu | Et | 0 | |
| 6-33 | Me | Et | 1 | |
| 6-34 | Et | Et | 1 | |
| 6-35 | n-Pr | Et | 1 | |
| 6-36 | i-Pr | Et | 1 | |
| 6-37 | n-Bu | Et | 1 | |
| 6-38 | i-Bu | Et | 1 | |
| 6-39 | s-Bu | Et | 1 | |
| 6-40 | t-Bu | Et | 1 | |
| 6-41 | Me | Et | 2 | |
| 6-42 | Et | Et | 2 | |
| 6-43 | n-Pr | Et | 2 | |
| 6-44 | i-Pr | Et | 2 | |
| 6-45 | n-Bu | Et | 2 | |
| 6-46 | i-Bu | Et | 2 | |
| 6-47 | s-Bu | Et | 2 | |
| 6-48 | t-Bu | Et | 2 | |

B. Formulation Examples

1. Dust

A dust is obtained by mixing 10 parts by weight of a compound of general formula (I) and 90 parts by weight of talc as inert substance and comminuting the mixture in a hammer mill.

2. Dispersible Powder

A wettable powder which is readily dispersible in water is obtained by mixing 25 parts by weight of a compound of general formula (I), 64 parts by weight of kaolin-containing quartz as inert material, 10 parts by weight of potassium lignosulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of general formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of general formula (I), 75 parts by weight of cyclohexanone as solvent and 10 parts by weight of oxethylated nonylphenol as emulsifier.

5. Water-Dispersible Granules

Water-dispersible granules are obtained by mixing

| | | |
|---|---|---|
| 75 | parts by weight of | a compound of general formula (I), |
| 10 | " | calcium lignosulfonate, |
| 5 | " | sodium lauryl sulfate, |
| 3 | " | polyvinyl alcohol and |
| 7 | " | kaolin, | grinding the mixture in a pinned-disk mill and granulating the powder in a fluidized bed by spraying on water as granulation liquid.

Water-dispersible granules are also obtained by homogenizing and precomminuting, in a colloid mill,

| | | |
|---|---|---|
| 25 | parts by weight of | a compound of general formula (I), |
| 5 | " | sodium 2,2'-dinaphthylmethane-6,6'-disulfonate, |
| 2 | " | sodium oleoylmethyltauride, |
| 1 | " | polyvinyl alcohol, |
| 17 | " | calcium carbonate and |
| 50 | " | water, | subsequently grinding the mixture in a bead mill, and atomizing and drying the resulting suspension in a spray tower by means of a single-substance nozzle.

C. Biological Examples

1. Pre-Emergence Herbicidal Action Against Harmful Plants

Seeds or rhizome pieces of mono- and dicotyledonous harmful plants are placed in sandy loam in pots of a diameter of 9 to 13 cm and covered with soil. The herbicides, formulated as emulsifiable concentrates or dusts, are applied to the surface of the covering soil in the form of aqueous dispersions or suspensions or emulsions at an application rate of 300 to 800 l of water/ha (converted), at various dosages. For further cultivation of the plants, the pots are then kept in a greenhouse under optimum conditions. The visual scoring of the damage to the harmful plants is carried out 3-4 weeks after the treatment. As shown by the results of these comparative tables, the selected compounds according to the invention have better herbicidal activity against a broad spectrum of economically important mono- and dicotyledonous harmful plants than the compounds disclosed in the prior art.

2. Post-Emergence Herbicidal Action Against Harmful Plants

Seeds of mono- and dicotyledonous harmful plants are placed in sandy loam in cardboard pots, covered with soil and grown in the greenhouse under good growth conditions. Two to three weeks after sowing, the test plants are treated at the three-leaf stage. The compounds according to the invention, which are formulated as wettable powders or as emulsion concentrates, are sprayed at an application rate of 600 to 800 l of water/ha (converted) in a dosage stated in tables 1 to 5 onto the surface of the green plant parts. After the test plants have been left to stand in the greenhouse for 3 to 4 weeks under optimum growth conditions, the action of the compounds according to the invention is scored in comparison to compounds disclosed in the prior art. As shown by the results of these comparison tables, the selected compounds according to the invention have better herbicidal activity against a broad spectrum of economically important mono- and dicotyledonous harmful plants than the compounds disclosed in the prior art.

Meanings of the abbreviations used in the comparison tables below:

| | | | |
|---|---|---|---|
| ABUTH | *Abutilon theophrasti* | AMARE | *Amaranthus retroflexus* |
| AVEFA | *Avena fatua* | DIGSA | *Digitaria sanguinalis* |
| ECHCG | *Echinochloa crus galli* | GALAP | *Galium aparine* |
| LOLMU | *Lolium multiflorum* | MATIN | *Matricaria inodora* |
| POLCO | *Polygonum convolvulus* | SETVI | *Setaria viridis* |
| STEME | *Stellaria media* | VERPE | *Veronica persica* |
| VIOTR | *Viola tricolor* | XANST | *Xanthium strumarium* |

COMPARATIVE TABLE 1

| | Pre-emergence | | | |
|---|---|---|---|---|
| | | Dosage | Activity against harmful plants | | |
| Compound No. | | [g a.i./ha] | ECHCG | LOLMU | ABUTH |
| 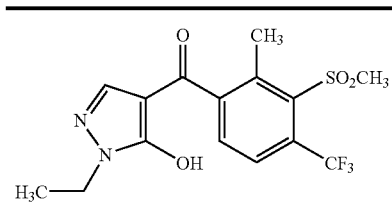 Compound according to the invention | | 80 | 100% | 70% | 100% |

COMPARATIVE TABLE 1-continued

Pre-emergence

| Compound No. | Dosage [g a.i./ha] | Activity against harmful plants | | |
|---|---|---|---|---|
| | | ECHCG | LOLMU | ABUTH |
| 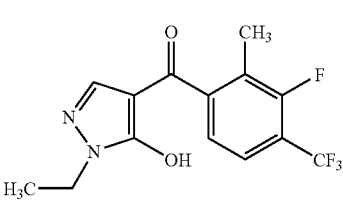<br>Compound known from the prior art | 80 | 30% | 0% | 0% |

COMPARATIVE TABLE 2

Pre-emergence

| Compound No. | Dosage [g a.i./ha] | Activity against harmful plants | | |
|---|---|---|---|---|
| | | AMARE | STEME | VERPE |
| Compound according to the invention | 80 | 90% | 90% | 90% |
| Compound known from the prior art | 80 | 0% | 40% | 0% |

COMPARATIVE TABLE 3

Post-emergence

| Compound No. | Dosage [g a.i./ha] | Activity against harmful plants | | |
|---|---|---|---|---|
| | | ECHCG | LOLMU | SETVI |
| 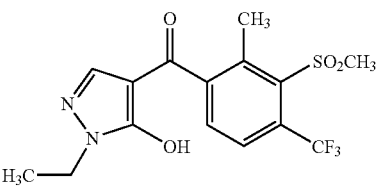<br>Compound according to the invention | 80 | 90% | 60% | 100% |

COMPARATIVE TABLE 3-continued

Post-emergence

| Compound No. | Dosage [g a.i./ha] | Activity against harmful plants | | |
|---|---|---|---|---|
| | | ECHCG | LOLMU | SETVI |

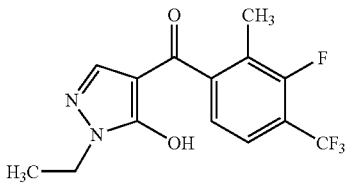

Compound known from the prior art

| | 80 | 0% | 0% | 0% |

COMPARATIVE TABLE 4

Port-emergence

| Compound No. | Dosage [g a.i./ha] | Activity against harmful plants | | |
|---|---|---|---|---|
| | | ABUTH | AMARE | MATIN |

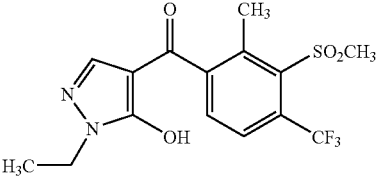

Compound according to the invention

| | 80 | 90% | 100% | 90% |

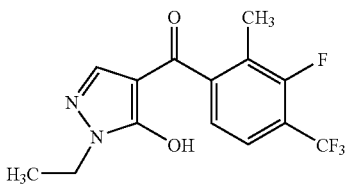

Compound known from the prior art

| | 80 | 80% | 0% | 0% |

COMPARATIVE TABLE 5

Port-emergence

| Compound No. | Dosage [g a.i./ha] | Activity against harmful plants | | | |
|---|---|---|---|---|---|
| | | POLCO | STEME | VERPE | VIOTR |

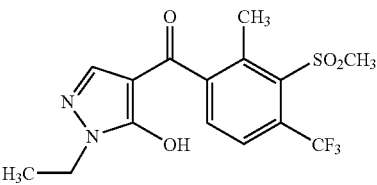

Compound according to the invention

| | 80 | 100% | 90% | 90% | 80% |

COMPARATIVE TABLE 5-continued

Post-emergence

| Compound No. | Dosage [g a.i./ha] | Activity against harmful plants | | | |
|---|---|---|---|---|---|
| | | POLCO | STEME | VERPE | VIOTR |
| 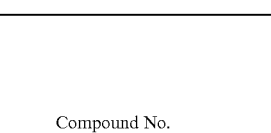<br>Compound known from the prior art | 80 | 60% | 0% | 0% | 0% |

COMPARATIVE TABLE 6

Pre-emergence

| Compound No. | Dosage [g a.i./ha] | Activity against harmful plants | | | |
|---|---|---|---|---|---|
| | | AVESA | LOLMU | SETVI | AMARE |
| Compound according to the invention | 320 | 90% | 90% | 100% | 100% |
| Compound known from the prior art | 320 | 20% | 20% | 20% | 50% |

COMPARATIVE TABLE 7

Post-emergence

| Compound No. | Dosage [g a.i./ha] | Activity against harmful plants | | | |
|---|---|---|---|---|---|
| | | AVESA | ECHCG | LOLMU | SETVI |
| Compound according to the invention | 80 | 70% | 90% | 80% | 90% |

COMPARATIVE TABLE 7-continued

Post-emergence

| Compound No. | Dosage [g a.i./ha] | Activity against harmful plants | | | |
|---|---|---|---|---|---|
| | | AVESA | ECHCG | LOLMU | SETVI |
| 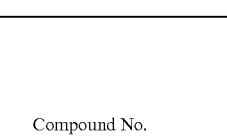<br>Compound known from the prior art | 320 | 20% | 0% | 20% | 30% |

COMPARATIVE TABLE 8

Pre-emergence

| Compound No. | Dosage [g a.i./ha] | Activity against harmful plants | | |
|---|---|---|---|---|
| | | LOLMU | GALAP | POLCO |
| (Compound according to the invention) | 80 | 70% | 80% | 50% |
| (Compound known from the prior art) | 80 | 0% | 60% | 30% |

COMPARATIVE TABLE 9

Pre-emergence

| Compound No. | Dosage [g a.i./ha] | Activity against harmful plants | | |
|---|---|---|---|---|
| | | VERPE | VIOTR | XANST |
| 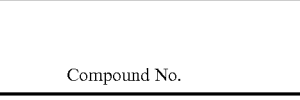<br>Compound according to the invention | 80 | 90% | 90% | 100% |

COMPARATIVE TABLE 9-continued

| | Pre-emergence | | | |
|---|---|---|---|---|
| | Dosage | Activity against harmful plants | | |
| Compound No. | [g a.i./ha] | VERPE | VIOTR | XANST |
| 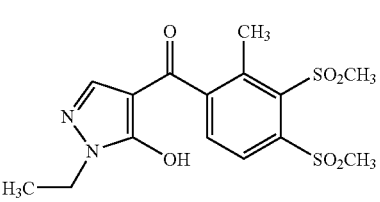<br>Compound known from the prior art | 80 | 80% | 20% | 40% |

COMPARATIVE TABLE 10

| | Post-emergence | | | | |
|---|---|---|---|---|---|
| | Dosage | Activity against harmful plants | | | |
| Compound No. | [g a.i./ha] | DIGSA | ECHCG | LOLMU | SETVI |
| Compound according to the invention | 80 | 100% | 90% | 60% | 100% |
| Compound known from the prior art | 80 | 80% | 80% | 20% | 80% |

COMPARATIVE TABLE 11

| | Post-emergence | | | | |
|---|---|---|---|---|---|
| | Dosage | Activity against harmful plants | | | |
| Compound No. | [g a.i./ha] | MATIN | VERPR | VIOTR | XANST |
| 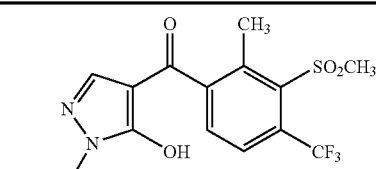<br>Compound according to the invention | 80 | 90% | 90% | 80% | 100% |

COMPARATIVE TABLE 11-continued

| | | Post-emergence | | | |
|---|---|---|---|---|---|
| | Dosage | Activity against harmful plants | | | |
| Compound No. | [g a.i./ha] | MATIN | VERPR | VIOTR | XANST |
| 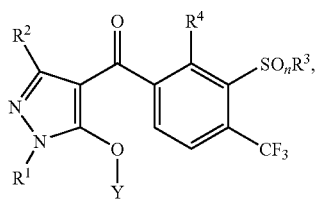<br>Compound known from the prior art | 80 | 40% | 80% | 50% | 70% |

The invention claimed is:

1. A 4-(4-trifluoromethyl-3-thiobenzoyl)pyrazole of the formula (I), or a salt thereof (I)

in which
$R^1$ is $(C_1-C_4)$-alkyl,
$R^2$ is hydrogen or $(C_1-C_4)$-alkyl,
$R^3$ is $(C_1-C_4)$-alkyl,
$R^4$ is $(C_1-C_4)$-alkyl,
Y is hydrogen, $(C_1-C_6)$-alkylsulfonyl, $(C_1-C_4)$-alkoxy-$(C_1-C_6)$-alkylsulfonyl, or is phenylsulfonyl, thiophenyl-2-sulfonyl, benzoyl, benzoyl-$(C_1-C_6)$-alkyl or benzyl, each of which is substituted by m identical or different radicals selected from the group consisting of halogen, $(C_1-C_4)$-alkyl and $(C_1-C_4)$-alkoxy,
m is 0, 1, 2 or 3,
n is 0, 1 or 2.

2. The 4-(4-trifluoromethyl-3-thiobenzoyl)pyrazole of the formula (I) or a salt thereof as claimed in claim 1 in which
$R^1$ is methyl or ethyl,
$R^2$ is hydrogen, methyl or ethyl,
$R^3$ is methyl or ethyl,
$R^4$ is methyl or ethyl,
Y is hydrogen, $(C_1-C_3)$-alkylsulfonyl, $(C_1-C_2)$-alkoxy-$(C_1-C_4)$-alkylsulfonyl, or is phenylsulfonyl, thiophenyl-2-sulfonyl, benzoyl, benzoyl-$(C_1-C_6)$-alkyl or benzyl, each of which is substituted by m methyl groups,
m is 0 or 1,
n is 0, 1 or 2.

3. The 4-(4-trifluoromethyl-3-thiobenzoyl)pyrazole of the formula (I) or a salt thereof as claimed in claim 1 in which
$R^1$ is methyl or ethyl,
$R^2$ is hydrogen, methyl or ethyl,
$R^3$ is methyl or ethyl,
$R^4$ is methyl or ethyl,
Y is hydrogen,
n is 0, 1 or 2.

4. A herbicidal composition which comprises a herbicidally effective amount of at least one compound of the formula (I) or a salt thereof as claimed in claim 1.

5. The herbicidal composition as claimed in claim 4 as a mixture with formulation auxiliaries.

6. A method for controlling unwanted plants which comprises applying an effective amount of at least one compound of the formula (I) or a salt thereof as claimed in claim 1 to the plants or a site of unwanted plant growth.

7. A method for controlling unwanted plants comprising using a compound of formula (I) or a salt thereof of claim 1.

8. The method as claimed in claim 7 wherein the compounds of the formula (I) or a salt thereof are used for controlling unwanted plants in crops of useful plants.

9. The method as claimed in claim 8 wherein the useful plants are transgenic useful plants.

10. A method for controlling unwanted plants which comprises applying an effective amount of a herbicidal composition as claimed in claim 4 to the plants or a site of unwanted plant growth.

11. The 4-(4-trifluoromethyl-3-thiobenzoyl)pyrazole of formula (I) or a salt thereof according to claim 1, wherein $R^1$ is methyl.

12. The 4-(4-trifluoromethyl-3-thiobenzoyl)pyrazole of formula (I) or a salt thereof according to claim 1, wherein $R^2$ is hydrogen.

13. The 4-(4-trifluoromethyl-3-thiobenzoyl)pyrazole of formula (I) or a salt thereof according to claim 1, wherein $R^3$ is methyl.

14. The 4-(4-trifluoromethyl-3-thiobenzoyl)pyrazole of formula (I) or a salt thereof according to claim 1, wherein $R^4$ is methyl.

15. The 4-(4-trifluoromethyl-3-thiobenzoyl)pyrazole of formula (I) or a salt thereof according to claim 1, wherein Y is hydrogen.

16. The 4-(4-trifluoromethyl-3-thiobenzoyl)pyrazole of formula (I) or a salt thereof according to claim 1, wherein n is 2.

17. The 4-(4-trifluoromethyl-3-thiobenzoyl)pyrazole of formula (I) or a salt thereof according to claim 1, wherein
$R^1$ is methyl;
$R^2$ is hydrogen;
$R^3$ is methyl;
$R^4$ is methyl;
Y is hydrogen; and
n is 2.

18. A method for controlling unwanted plants comprising using a compound of formula (I) or a salt thereof of claim 17.

19. A herbicidal composition comprising a herbicidally effective amount of a compound of the formula (I) or a salt thereof as claimed in claim 17.

20. The 4-(4-trifluoromethyl-3-thiobenzoyl)pyrazole of formula (I) or a salt thereof according to claim 1, wherein
$R^1$ is ethyl;
$R^2$ is hydrogen;
$R^3$ is methyl;
$R^4$ is methyl;
Y is hydrogen; and
n is 2.

* * * * *